United States Patent
Kota et al.

(10) Patent No.: US 10,442,166 B2
(45) Date of Patent: Oct. 15, 2019

(54) HYDROPHILIC, YET SLIPPERY SOLID SURFACES

(71) Applicant: Colorado State University Research Foundation, Fort Collins, CO (US)

(72) Inventors: Arun K. Kota, Fort Collins, CO (US); Hamed Vahabi, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 16/246,136

(22) Filed: Jan. 11, 2019

(65) Prior Publication Data
US 2019/0152201 A1 May 23, 2019

Related U.S. Application Data

(63) Continuation of application No. PCT/US2018/054613, filed on Oct. 5, 2018.
(Continued)

(51) Int. Cl.
*B32B 27/08* (2006.01)
*A61L 29/08* (2006.01)
(Continued)

(52) U.S. Cl.
CPC ............ *B32B 27/08* (2013.01); *A61L 29/08* (2013.01); *A61L 33/00* (2013.01); *B32B 3/30* (2013.01);
(Continued)

(58) Field of Classification Search
CPC ......... B32B 27/08; B32B 3/30; B32B 27/283; B32B 27/285; B32B 2307/728;
(Continued)

(56) References Cited

U.S. PATENT DOCUMENTS

| 4,906,237 A | 3/1990 | Johansson et al. |
| 5,662,960 A | 9/1997 | Hostettler et al. |

(Continued)

FOREIGN PATENT DOCUMENTS

WO 0127174 A1 4/2001

OTHER PUBLICATIONS

Acres et al., "Molecular Structure of 3-Aminopropyltriethoxysilane Layers Formed on Silanol-Terminated Silicon Surfaces," J. Phys. Chem. C., 116(10):6289-6297, Feb. 2012.
(Continued)

*Primary Examiner* — Ling Siu Choi
*Assistant Examiner* — Ronald Grinsted
(74) *Attorney, Agent, or Firm* — Haukaas Fortius PLLC; Michael H. Haukaas (57) ABSTRACT

In this work, a hydrophilic, yet slippery solid surface was developed. Because the surfaces are hydrophilic, there is significant affinity between the surface and contacting water, which results in substantial spreading of the contacting liquids on the surface. Due to their strong affinity, a high solid-liquid adhesion having virtually no mobility of the water on the surface occurs. However, counter-intuitively, the disclosed surfaces are highly slippery such that liquids can slide on the surface while maintaining their hydrophilicity. Demonstrated herein are water droplets that can slide on the surface under its own weight, when the hydrophilic, yet slippery solid surface is slightly tilted ($\omega=3°$). This indicates that the disclosed hydrophilic surfaces are slippery to water.

22 Claims, 5 Drawing Sheets

Related U.S. Application Data (60) Provisional application No. 62/572,042, filed on Oct. 13, 2017.

(51) Int. Cl.

| | | |
|---|---|---|
| *A61L 33/00* | (2006.01) | |
| *B32B 3/30* | (2006.01) | |
| *B32B 27/28* | (2006.01) | |
| *C08G 65/336* | (2006.01) | |
| *C08L 71/02* | (2006.01) | |
| *C08L 71/08* | (2006.01) | |
| *C08L 83/04* | (2006.01) | |
| *B05D 3/10* | (2006.01) | |
| *B05D 5/08* | (2006.01) | |
| *B05D 1/18* | (2006.01) | |

(52) U.S. Cl.
CPC ............ *B32B 27/28* (2013.01); *B32B 27/283* (2013.01); *B32B 27/285* (2013.01); *C08G 65/336* (2013.01); *C08L 71/02* (2013.01); *C08L 71/08* (2013.01); *C08L 83/04* (2013.01); *B05D 1/18* (2013.01); *B05D 3/10* (2013.01); *B05D 5/08* (2013.01); *B32B 2307/728* (2013.01); *B32B 2307/746* (2013.01); *B32B 2535/00* (2013.01); *C08L 2203/02* (2013.01)

(58) Field of Classification Search
CPC .......... B32B 2307/746; B32B 2535/00; B32B 27/28; C08L 71/08; C08L 83/04; C08L 2203/02; C08L 71/02; A61L 29/08; A61L 33/00; C08G 65/336; B05D 1/18; B05D 3/10; B05D 5/08
USPC ........................................................ 427/352
See application file for complete search history.

(56) References Cited

U.S. PATENT DOCUMENTS

| | | |
|---|---|---|
| 6,080,488 A | 6/2000 | Hostettler et al. |
| 2006/0088666 A1 | 4/2006 | Kobrin et al. |
| 2008/0206752 A1* | 8/2008 | Balakirev .................. C08J 7/18 435/6.11 |
| 2011/0311769 A1 | 12/2011 | Chen et al. |

OTHER PUBLICATIONS

Drelich et al., "Hydrophilic and Superhydrophilic Surfaces and Materials," Soft Matter, 21(7):9804-9828, Aug. 2011.

Drelich et al., "Physics and Applications of Superhydrophobic and Superhydrophilic Surfaces and Coatings," Surface Innovations, 2(4):211-227, Oct. 2014.

Ho et al., "Liquid Water can Slip on a Hydrophilic Surface," PNAS, 108(39):16170-16175, Sep. 2011.

International Search Report and Written Opinion of the ISA/US dated Dec. 14, 2018 in International Application No. PCT/US2018/054613; 7pgs.

Jones et al., "Revolutionary Future Uses of Contact Lenses," Optom Vis Sci., 93(4):325-327, Apr. 2016.

Ketelson et al., "Dynamic Wettability Properties of a Soft Contact Lens Hydrogel," Colloids Surf B Biointerfaces, 40 (1):1-9, Jan. 2005.

Ko et al., "Hydrophilic Surface Modification of Poly(Methyl Methacrylate)-Basedocular Prostheses Using Poly(Ethylene Glycol) Grafting," Colloids Surf B Biointerfaces, 158:287-294, Oct. 2017.

Kopeček J., "Hydrogels from Soft Contact Lenses and Implants to Self-Assembled Nanomaterials," J Polym Sci A Polym Chem., 47(22):5929-5946, Nov. 2009.

Li et al., "Making Polymeric Membranes Antifouling via "Grafting From" Polymerization of Zwitterions," J. Appl. Polym. Sci., 132(21):41781, Dec. 2014.

Ma et al., "Elucidating the Mechanism of Silica Nanoparticle PEGylation Processes Using Fluorescence Correlation Spectroscopies," Chem. Mater., 28(5):1537-1545, Feb. 2016.

Vogler E., "Protein Adsorption in Three Dimensions," Biomaterials, 33(5):1201-1237, Feb. 2012.

\* cited by examiner

HYDROPHILIC, YET SLIPPERY SOLID SURFACES

RELATED APPLICATIONS

This application is a continuation under 35 U.S.C. 111(a) of International Patent Application No. PCT/US2018/054613, filed Oct. 5, 2018, which claims priority under 35 U.S.C. § 119(e) to U.S. Provisional Patent Application No. 62/572,042, filed Oct. 13, 2017, which applications are incorporated herein by reference.

GOVERNMENT SUPPORT

This invention was made with government support under grants R01 HL135505 and R21 HL139208 awarded by National Institutes of Health and grant 1751628 awarded by National Science Foundation. The government has certain rights in the invention.

BACKGROUND OF THE INVENTION

Engineering of the interface of a solid surface with contacting liquids to increase the liquid mobility is of great interest due to its broad technological implications ranging from biomedical to mechanical applications. Recent years have seen rapid and noticeable advances in the design and fabrication of super-repellent surfaces as well as lubricant-infused surfaces as two different approaches in solving this extremely challenging problem. Super-repellent surfaces, relying on an air layer trapped at the solid-liquid interface, while promising, suffer from inherent limitations that severely restrict their applicability. Repellency on such surfaces is prone to failure under pressure; retaining the repellency against low surface tension liquids entails the incorporation of complex (and usually fragile) topographic features with fabrication and scalability problems; surfaces are not fully transparent; and the surfaces can be fouled by contaminants. Similarly, despite their great potentials, lubricant-infused surfaces have not been considered a viable solution since their performance can be threatened over time by lubricant evaporation or its loss under flow conditions.

Figure 1:
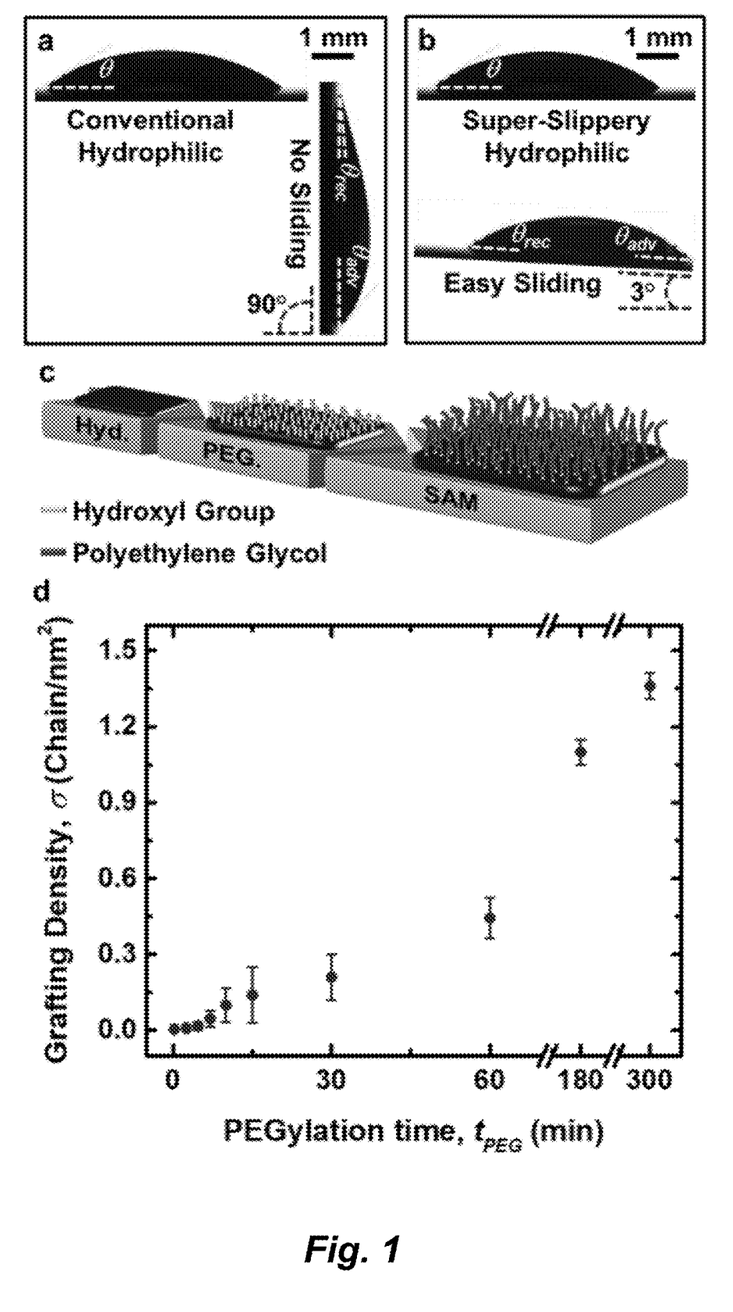
FIG. 1. Fabrication of the hydrophilic, yet slippery solid surfaces: a) A water droplet on a conventional hydrophilic surface (the droplet cannot slide on the surface even if it is tilted by 90°); b) A water droplet on a hydrophilic, yet slippery solid surface (the droplet can easily slide on the surface); c) Schematic of the fabrication process of hydrophilic, yet slippery solid surfaces; d) Variation of the grafting density σ by PEGylation time $t_{PEG}$; e) Variation of the contact angle θ by PEGylation time $t_{PEG}$; f) Variation of the sliding angle ω by PEGylation time $t_{PEG}$. Inset shows the sliding angle ω surfaces with very low inter-tether distance. Volume of the test droplets≈20 μl.

In a new direction, recently, nearly smooth solid surfaces grafted with covalently attached flexible hydrophobic groups have shown high slipperiness against contacting liquids. However, utilization of these surfaces in biomedical applications is highly restricted due to their vulnerability against fouling (induced by their hydrophobic nature). As well, performance of such surfaces in condensation heat transfer is debatable due to the low nucleation rate on hydrophobic surfaces. In striking contrast, hydrophilic surfaces (i.e., surfaces with contact angle θ<90°, see FIG. 1a) have attracted tremendous interest in such applications due to their superior antifouling capability and high nucleation rates. However, lack of slipperiness on conventional hydrophilic solid surfaces (see FIG. 1a, a water droplet cannot slide on a hydrophilic surface even when it is tilted by 90°) hinders the utilization of such surfaces in many applications.

While there are no prior experimental reports on hydrophilic, yet slippery solid surfaces, recent molecular dynamics simulations have demonstrated that hydrophilic surfaces with very high physical homogeneity (i.e., negligible surface roughness), very high chemical homogeneity (i.e., highly uniform distribution of hydrophilic molecules on the surface) and sufficiently low inter-tether distance D allow water molecules to smoothly slide past the surfaces. Although slippery surfaces that are hydrophobic and lubricated have been fabricated before, the materials and methods to experimentally fabricate slippery solid surfaces that are hydrophilic have never been disclosed. Therefore, there is a need for fabricated hydrophilic and slippery surfaces.

SUMMARY

This disclosure provides a novel hydrophilic solid surface that is slippery. These hydrophilic, yet slippery solid surfaces were prepared using a fabrication technique described as a "grafting to" technique, which is significantly less complex compared to a "grafting from" technique. Using this technique, physically and chemically homogeneous hydrophilic surfaces composed of low molecular weight PEG brushes with an ultra-high grafting density (i.e., low inter-tether distance D) have been fabricated. Additionally, these hydrophilic, yet slippery solid surfaces show sustained dropwise condensation (relying on extremely slippery nature of the surface) that can lead to significantly higher condensation heat transfer coefficient. Also, the hydrophilic, yet slippery solid surfaces show outstanding fouling resistance to protein adsorption.

Accordingly, this disclosure provides a hydrophilic and slippery layer comprising a substrate surface covalently bonded to polyethylene glycol brushes via O—Si bonds wherein the substrate surface and brushes form a hydrophilic and slippery layer, the brushes have an inter-tether distance (D) of less than about 20 nanometers, and the surface of the hydrophilic and slippery layer has a root mean square surface roughness ($R_{rms}$) of less than about 10 nanometers.

In some embodiments of the hydrophilic and slippery layer disclosed herein, the brushes are a moiety of Formula I:

wherein, for a majority of brushes
R is —CH$_3$ or —CH$_2$CH$_3$;
m is 0-2; and
n is 2-1000.

Additionally, this disclosure provides a method of forming a hydrophilic and slippery surface comprising:
a) immersing a substrate having a hydroxylated surface in a solution consisting essentially of a PEG silane for a sufficient amount of time to covalently bond the PEG silane to the hydroxylated surface to form PEG brushes on the substrate; and
b) washing the PEG brushes with water to remove excess PEG silane, thereby providing a hydrophilic and slippery surface that has a root mean square surface roughness ($R_{rms}$) of less than about 10 nanometers;
wherein the hydroxylated surface is covalently bonded to the PEG brushes via O—Si bonds, and the PEG brushes have an inter-tether distance (D) of less than about 20 nanometers.

This disclosure also provides a composition comprising a hydrophilic and slippery layer according to the disclosure herein and a substrate comprising a biomedical implant or device such as a contact lens.

Also, this disclosure provides a method of transferring heat comprising:

a) condensing an aqueous substance on the surface of the hydrophilic and slippery layer disclosed herein, wherein the condensed aqueous substance forms droplets on the surface of the hydrophilic and slippery layer; and b) removing the droplets under an accelerating force;

wherein the droplets are removed by sliding off the surface of the hydrophilic and slippery layer thereby transferring heat away from the aqueous substance.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 3. a and b) Protein adsorption on an extremely hydrophilic non-slippery surface and a hydrophobic slippery surface, respectively at the onset of exposure to fibrinogen. The background represents proteins and black represents the areas free of protein. Protein adsorbs significantly on these surfaces; c) Protein adsorption on hydrophilic, yet slippery solid surface after 20 h exposure to fibrinogen. Virtually no protein is adsorbed on the surface after 20 h exposure. d) Inset illustrates that even after 20 h the rate of adsorption on the surface is very slow; e-g) Dropwise condensation on a hydrophilic non-slippery surface, hydrophobic slippery surface, and hydrophilic, yet slippery solid surface, respectively. No droplet sliding was observed on hydrophilic non-slippery surface resulting in transition to a film-wise regime with low heat transfer coefficient. Only one droplet slides on the hydrophobic slippery surface indicating slow nucleation rate and slow droplet growth resulting in low heat transfer coefficient. Prompt droplet nucleation, growth and removal on the hydrophilic, yet slippery solid surface results in sustained dropwise condensation with significantly higher heat transfer coefficient.

DETAILED DESCRIPTION

There have been many strategies to prepare slippery surfaces (i.e., surfaces that display high mobility to liquid droplets). One strategy, inspired by lotus leaves, is the fabrication of superhydrophobic coatings/surfaces. The simultaneous incorporation of topographic features (i.e., microscale and nanoscale texture) and low surface energy chemistry has been the strategy to maintain an air layer at solid-liquid interface and thus enhance the surface repellency. An inherent problem with this approach is that at sufficiently high pressure, breakthrough of the liquid into the surface texture occurs resulting in failure of the repellency. Another drawback of this strategy is their poor durability (i.e., the textures are usually fragile or loosely adhered to the surface).

A second strategy to impart the slipperiness to the surface involves employing lubricated surfaces (with liquid lubricants). When a liquid droplet comes in contact with a lubricated surface, a liquid-lubricant (i.e., liquid-liquid) interface forms, instead of a liquid-solid interface. Such liquid-liquid interfaces display very low adhesion and high mobility of the droplets on the lubricated surfaces. However, lubricated surfaces suffer from depletion of lubricant over time, either by evaporation or by removal of lubricant along with the moving liquid.

A third strategy to impart slipperiness to the surface involves covalently bonding liquid-like hydrophobic brushes (e.g., PDMS brushes). The liquid-like hydrophobic brushes are highly flexible due to their rotational and/or bending motions. Although such surfaces may be more durable than the lubricated surfaces, water displays high contact angles on such surfaces because they are hydrophobic.

However, there are no known solid surfaces that are hydrophilic, yet slippery. Such counter-intuitive surfaces have significant potential applications in enhanced condensation heat transfer, reduced protein adsorption, improved contact lens comfort, etc.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* $14^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

This disclosure provides methods of making the compounds and compositions of the invention. The compounds and compositions can be prepared by any of the applicable techniques described herein, optionally in combination with standard techniques of organic synthesis. Many techniques such as etherification and esterification are well known in the art. However, many of these techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as March's Advanced Organic Chemistry: Reactions, Mechanisms, and Structure, 5th Ed., by M. B. Smith and J. March (John Wiley & Sons, New York, 2001); Comprehensive Organic Synthesis. Selectivity, Strategy & Efficiency in Modern Organic Chemistry. In 9 Volumes, Barry M. Trost, Editor-in-Chief (Pergamon Press, New York, 1993 printing); Advanced Organic Chemistry, Part B: Reactions and Synthesis, Second Edition, Cary and Sundberg (1983);

The formulas and compounds described herein can be modified using protecting groups. Suitable amino and carboxy protecting groups are known to those skilled in the art (see for example, Protecting Groups in Organic Synthesis, Second Edition, Greene, T. W., and Wutz, P. G. M., John Wiley & Sons, New York, and references cited therein;

Philip J. Kocienski; Protecting Groups (Georg Thieme Verlag Stuttgart, New York, 1994), and references cited therein); and Comprehensive Organic Transformations, Larock, R. C., Second Edition, John Wiley & Sons, New York (1999), and referenced cited therein.

As used herein, the term "substituted" or "substituent" is intended to indicate that one or more (for example, 1-20 in various embodiments, 1-10 in other embodiments, 1, 2, 3, 4, or 5; in some embodiments 1, 2, or 3; and in other embodiments 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms.

Embodiments of the Invention

This disclosure provides various embodiments of a hydrophilic and slippery layer comprising (or in some embodiments, consisting essentially of) a substrate surface covalently bonded to polyethylene glycol brushes via O—Si bonds wherein the substrate surface and brushes form a hydrophilic and slippery layer, the brushes have an inter-tether distance (D) of less than about 20 nanometers, and the surface of the hydrophilic and slippery layer has a root mean square surface roughness ($R_{rms}$) of less than about 10 nanometers.

In further embodiments, the brushes are a moiety of Formula I:

wherein, for a majority of brushes
R is —$CH_3$ or —$CH_2CH_3$;
m is 0-2; and
n is 2-1000.

In some embodiments, n of the majority of brushes is 2-10 or 6-9. In other embodiments, $R_{rms}$ is about 0.1 nanometers to about 0.3 nanometers. In other embodiments, $R_{rms}$ is less than about 4 nm, about 3 nm, about 2 nm, or about 1 nm. In yet other embodiments, the maximum chain length is about 3 nanometers (nm), about 6 nm, about 4 nm, about 2 nm, or about 1 nm. In additional embodiments, the inter-tether distance is less than about 5 nanometers. In other embodiments, the inter-tether distance is less than about 15 nm, about 10 nm, about 4 nm, about 3 nm, about 2 nm, about 1 nm, or about 0.5 nm, or about 0.1 nm to about 1.5 nm. In some further embodiments, the inter-tether distance is about 1 nanometer to about 3 nanometers.

In some other embodiments, the density of polyethylene glycol brushes is at least about 0.1 brushes per nanometer$^2$ of the substrate surface. In yet some other embodiments, the density is about 0.15 to about 1.5 brushes per nanometer$^2$ of the substrate surface. In other embodiments, the density is about 1.5 to about 5 brushes per nanometer$^2$ of the substrate surface.

This disclosure also provides a hydrophilic and slippery layer as disclosed above further comprising a hydration layer at the surface of the hydrophilic and slippery layer. In other various embodiments, the surface of the hydrophilic and slippery layer is slippery to a liquid comprising water. In yet other embodiments, the hydrophilic and slippery layer does not have a hydrophilic layer or does not have a lubricating layer. In some embodiments, the test liquid has a surface tension of more than about 30 mN m$^{-1}$, about 35 mN m$^{-1}$, about 40 mN m$^{-1}$, or about 45 mN m$^{-1}$, or about 5 mN m$^{-1}$ to about 50 mN m$^{-1}$.

In additional embodiments, a liquid on the surface of the hydrophilic and slippery layer has a contact angle, sliding angle, or a combination thereof that varies less than about 20% at a relative humidity of about 5% or more, or the variation is about 1% to about 15% and/or the relative humidity is about 1% to about 99%.

In various other embodiments, the surface of the hydrophilic and slippery layer resists adsorption or adhesion of a contaminant for about 1 hour or more of exposure (time) to the contaminant. In other embodiments the exposure is more than about 2 hours, about 4 hours, about 6 hours, about 8 hours, about 10 hours, about 12 hours, about 15 hours, about 20 hours, about 1 day, about 2 days, or about 1 week. In some other embodiments, the contaminant comprises a protein.

In additional embodiments, the hydrophilic and slippery layer is self-lubricating, or it can be non-lubricated. It is noted that self-lubrication is due to the hygroscopicity of the PEG brushes wherein water molecules (e.g., not oils, or lubricants that are not water) lubricate the surface of the hydrophilic and slippery layer. In further embodiments, the hydrophilic and slippery layer is about 60% to about 100% transparent to visible light. Typically, 100% transparency refers to about 99% to about 99.9% transparency.

This disclosure provides a method of forming a hydrophilic and slippery (solid) surface comprising:
a) immersing a substrate having a hydroxylated surface in a solution consisting essentially of a PEG silane for a sufficient amount of time (i.e., PEGylation time) to covalently bond the PEG silane to the hydroxylated surface to form PEG brushes on the substrate; and
b) washing the PEG brushes with water to remove excess PEG silane, thereby providing a hydrophilic and slippery surface that has a root mean square surface roughness ($R_{rms}$) of less than about 10 nanometers;
wherein the hydroxylated surface is covalently bonded to the PEG brushes via O—Si bonds, and the PEG brushes have an inter-tether distance (D) of less than about 20 nanometers.

In some embodiments, the poly(ethylene glycol)silane is grafted to the hydroxylated substrate surface (not grafted from the substrate). In other embodiments, the poly(ethylene glycol)silane is a 2-[methoxy (polyethyleneoxy)6-9propyl] trialkoxysilane. In additional embodiments, the hydrophilic and slippery surface has a root mean square surface roughness ($R_{rms}$) of about 0.1 nanometers to about 0.3 nanometers. In yet other embodiments, the hydrophilic and slippery surface has PEG brush density of at least about 0.1 brushes per nanometer. In further embodiments, the inter-tether distance (D) is less than about 3 nanometers.

In additional embodiments, a drop of water at the hydrophilic and slippery surface has a sliding angle (ω) of less than about 10 degrees. In other embodiments, the sliding angle is less than about 20 degrees, about 15 degrees, about 5 degrees, about 4 degrees, about 3 degrees, about 2 degrees, about 1 degree, or about 0.5 degrees.

This disclosure further provides a composition comprising a hydrophilic and slippery layer disclosed herein and a substrate comprising a biomedical implant or device (e.g., contact lens, stent, or a heart valve).

Also, this disclosure provides a method of transferring heat comprising:
a) condensing an aqueous substance on the surface of the hydrophilic and slippery layer disclosed herein, wherein the condensed aqueous substance forms droplets on the surface of the hydrophilic and slippery layer; and
b) removing the droplets under an accelerating force;
wherein the droplets are removed by sliding off the surface of the hydrophilic and slippery layer thereby transferring heat away from the aqueous substance.

In additional embodiments, the removal rate of the droplets on the surface of the hydrophilic and slippery layer is faster in comparison to the removal rate of aqueous droplets formed by condensing on hydrophobic and slippery surface, wherein the corresponding coefficient of heat transfer (h) for the surface of the hydrophilic and slippery layer is thereby higher than h for the hydrophobic and slippery surface, and wherein the accelerating force is the same for the comparison.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02. 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

RESULTS AND DISCUSSION

On conventional hydrophilic surfaces, droplets spread leading to a contact angle θ<90°, but droplets don't slide even if the surface is tilted (FIG. 1a). In striking contrast, on hydrophilic, yet slippery solid surfaces reported in this work, the contact angle θ<90 and the sliding angle is very low (ω~3°; FIG. 1b). It is important to note that these hydrophilic, yet slippery surfaces are all solid (i.e., non-porous). Further, these hydrophilic, yet slippery solid surfaces are unlike the SLIPS surfaces or lubricated surfaces, which consist of lubricants that can wear away easily and consequently have poor durability.

These hydrophilic, yet slippery solid surfaces were fabricated using a "grafting to" technique, consisting of an acid-catalyzed grafting of hydrophilic PEG brushes to very smooth surfaces of silicon wafer with sufficiently high grafting density (i.e., number of PEG brushes per unit area), resulting in low inter-tether distance D. The silicon wafer surfaces (FIG. 1c) were hydroxylated followed by PEGylation. Here, PEGylation refers to the grafting of the Polyethylene glycol brushes to the surface by dipping the hydroxylated surface in an aqueous solution of the PEG silane. A low molecular weight PEG silane (i.e., 2-[Methoxy (Polyethyleneoxy) 6-9propyl]Trimethoxysilane) was used in this work. The fabrication procedure is fairly simple and straightforward (i.e., no need for complex synthetic-chemistry techniques and equipment) and can be termed "instant" as it takes only a few minutes to fabricate a hydrophilic, yet slippery solid surface at room temperature.

As the PEGylation time $t_{PEG}$ increased, more PEG groups were grafted to the surface, thereby increasing the grafting density σ and decreasing the inter-tether distance D. The grafting density σ was determined as:

$$\sigma = \frac{h \rho N_A \times 10^{-21}}{M_n}. \quad \text{(Equation 1)}$$

Here h is the thickness of the PEG brushes on the solid surface measured using ellipsometry, ρ is the density of the bulk PEG at 293 K, NA is the Avogadro's number, and $M_n$ is the average molecular weight of PEG. After determining the grafting density σ, the corresponding inter-tether distance D was estimated as, $$D \sim \frac{2}{\sqrt{\pi \sigma}}$$

The disclosed results (FIG. 1d) indicate that the grafting density can be varied from very low (σ→0 Chain nm$^{-2}$) to very high (σ→1.4 Chain nm$^{-2}$) by increasing the PEGylation time $t_{PEG}$. This in turn varied the inter-tether distance (D) from very high (D→16 nm) to very low (D→0.9 nm).

Figure 2:
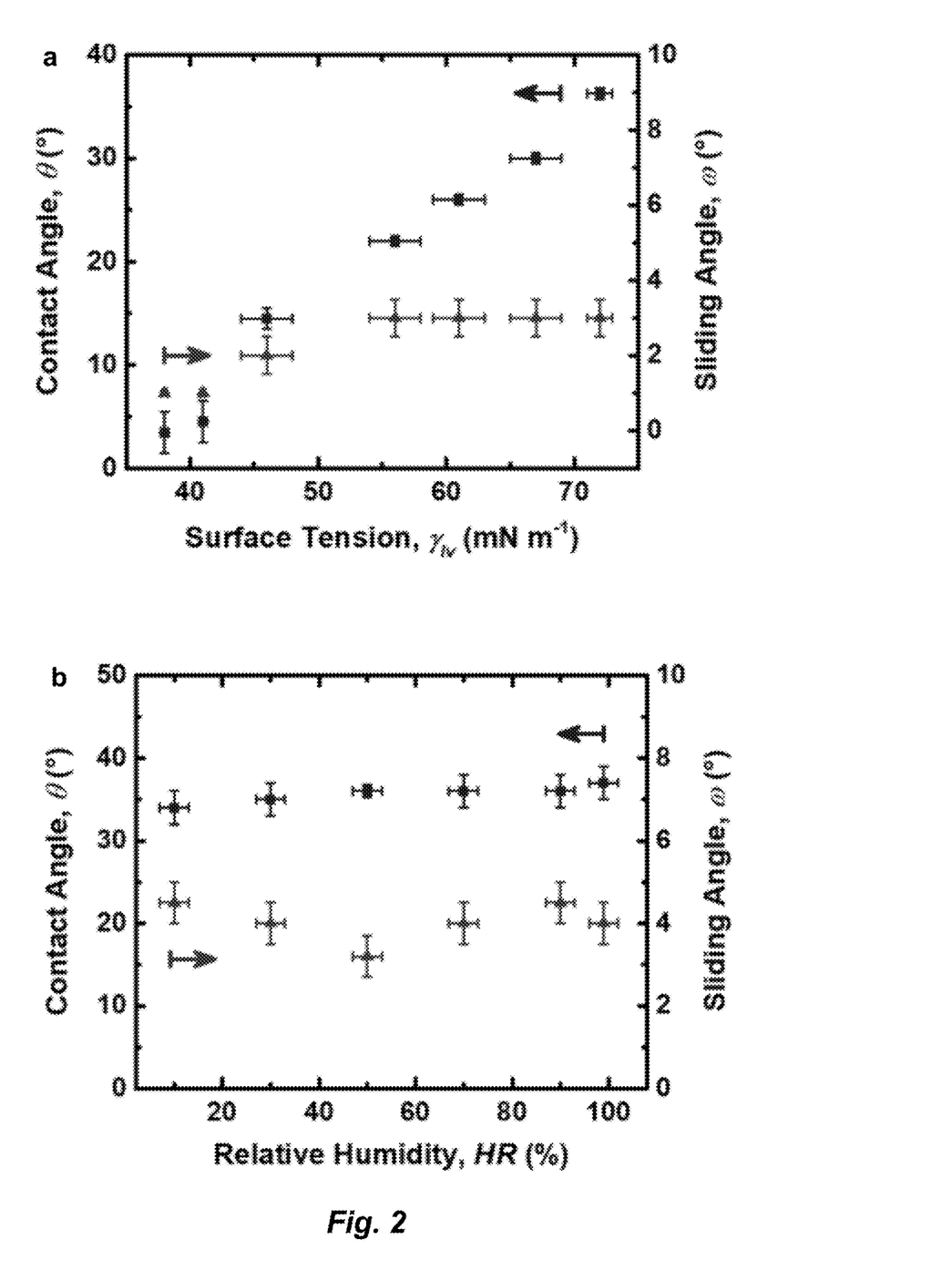
FIG. 2. Characteristics of the hydrophilic, yet slippery solid surfaces: a) Variation of the contact angle θ and the sliding angle ω by the surface tension of the test liquids $γ_{lv}$, indicative of the hydrophilic, yet slippery solid surfaces; b) Variation of the contact angle θ and the sliding angle ω by the relative humidity HR, indicative of the stability of the hydrophilic, yet slippery solid surfaces over a wide range of humidity.

At PEGylation time $t_{PEG}$=0 min, the grafting density σ=0 Chain nm$^{-2}$ and hydroxylated surface was covered primarily by hydroxyl groups (—OH). Since the hydroxyl groups are very hydrophilic, it resulted in substantial spreading of the water droplet on the surface (i.e., θ<5°). As the PEGylation time $t_{PEG}$ increased, the contact angle increased indicating that the PEG brushes (that are less hydrophilic compared to the hydroxyl groups) are increasingly being grafted to the surface (see FIG. 1e). Further, as the PEGylation time increased the sliding angle decreased (see FIG. 1f) indicating an increasing chemical homogeneity (i.e., increasing uniformity in surface coverage with PEG brushes). At very high PEGylation time (e.g., $t_{PEG}$=300 min), the grafting density of the PEG brushes is very high (i.e., σ→1.4 Chain nm$^{-2}$), resulting in a chemically homogeneous the surface that is virtually fully covered by PEG brushes. This high chemical homogeneity (due to the high grafting density) coupled with the high physical homogeneity (due to the low surface roughness of PEG brushes grafted to the silicon wafer) resulted in a contact angle θ≈36° for the water droplet (i.e., hydrophilic), with very low contact angle hysteresis. This very low contact angle hysteresis resulted in slipperiness with a sliding angle ω≤3°. In other words, the solid surface was hydrophilic, yet slippery. These hydrophilic, yet slippery solid surfaces displayed contact angles θ≤36° and sliding angles ω≤3° for aqueous solutions containing different concentrations of SDS with surface tension varying from 38 mN/m to 72 mN/m (FIG. 2a). Further, these hydrophilic, yet slippery solid surfaces displayed contact angles θ≈36° and sliding angles ω≈3° for water over a wide range of humidity from 10% to 100% (FIG. 2b).

It is hypothesized in this work that the hydrophilic, yet slippery solid surfaces will be very useful for two applications—first, to significantly reduce biofouling due to protein adsorption and second, to greatly increase heat transfer coefficient by enhancing droplet removal in condensation.

Figure 3:
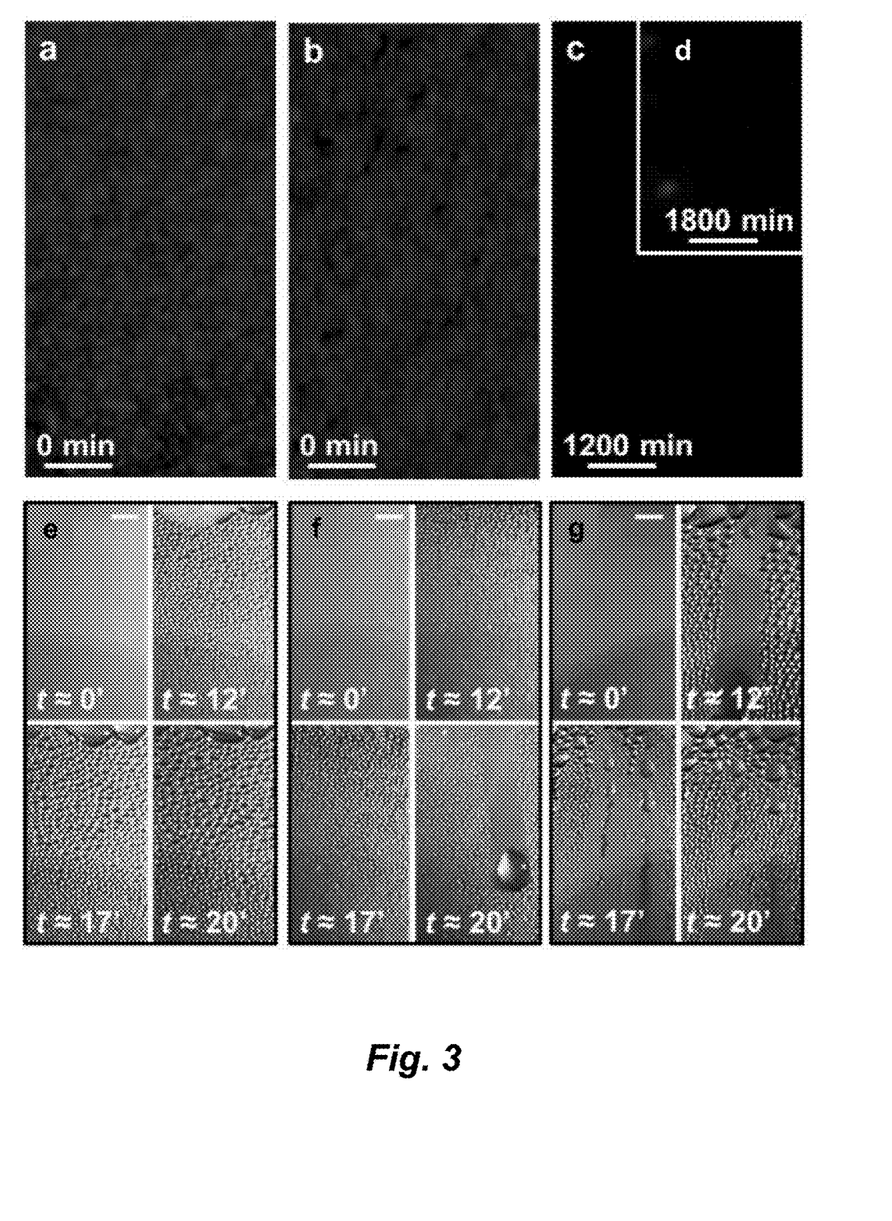
Figure 4:
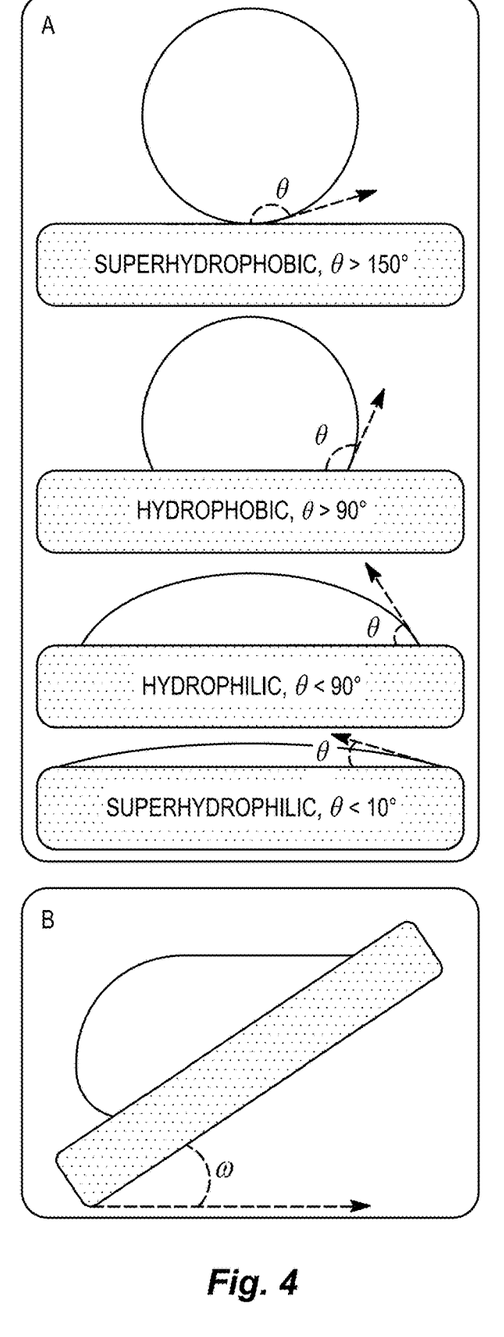
FIG. 4. Schematic of a) Contact angle on surfaces with different wettability; b) Sliding angle.

Reducing Protein Adsorption:

Typically, hydrophilic surfaces are considered to be more resistant to biofouling compared to hydrophobic surfaces. However, conventional hydrophilic surfaces, without slipperiness, lead to immobile liquid in the vicinity of the solid-liquid interface. As a result, proteins eventually diffuse and adsorb on conventional hydrophilic surfaces. In contrast, hydrophilic, yet slippery solid surfaces lead to highly mobile liquid in the vicinity of the solid-liquid interface. It is hypothesized that the highly mobile liquid in the vicinity of the solid-liquid interface not only impedes protein adsorption on the solid surface, but also enhances protein desorption from the solid surfaces. In order to test this hypothesis, three different surfaces—a conventional hydrophilic surface (FIG. 3a), a hydrophobic and slippery surface (FIG. 3b) and a hydrophilic, yet slippery solid surface (FIG. 3c)—were exposed to fibrinogen (a representative protein, labeled red in the figures) and the adsorption was characterized using total internal reflection fluorescence (TIRF) microscopy. The results indicated that protein adsorption occurs virtually instantaneously on the conventional hydrophilic surface (FIG. 3a) and the hydrophobic and slippery surface (FIG. 3b), but there is no protein adsorption even after an entire day on the hydrophilic, yet slippery solid surface. This is a staggering result given that proteins adsorb within a few minutes even on the state-of-the-art anti-biofouling surfaces. Due to their unprecedented anti-biofouling properties, the hydrophilic, yet slippery solid surfaces are anticipated to revolutionize the technological landscape for biomedical implants and devices, marine equipment and food-contacting and beverage-contacting devices and containers, where protein adsorption is a significant problem.

Enhancing Condensation Heat Transfer:

Condensation involves a phase change from vapor to the liquid. For efficient heat transfer, the condenser surface should allow rapid nucleation of liquid droplets from the surrounding vapor and also facilitate rapid removal of the condensed liquid droplets from the surface so that new vapor can contact and condense on the surface. Typically, hydrophilic surfaces (e.g., metallic surfaces) result in rapid nucleation of liquid droplets from the surrounding vapor and are preferred for condensation. However, conventional hydrophilic surfaces, without slipperiness, cannot facilitate rapid removal of condensed liquid droplets, i.e., condensed liquid droplets remain stuck to the surface and impede heat transfer because liquids possess poor thermal conductivity. In contrast, hydrophilic, yet slippery solid surfaces not only allow rapid nucleation of liquid droplets from the surrounding vapor, but also facilitate rapid removal of the condensed liquid droplets from the surface. In order to demonstrate this, three different vertical surfaces—a conventional hydrophilic surface (FIG. 3e), a hydrophobic and slippery surface (FIG. 3f) and a hydrophilic, yet slippery solid surface (FIG. 3g)—were exposed to water vapor. The results indicated that the many liquid droplets nucleate, but remain stuck on the conventional hydrophilic surface (FIG. 3e); fewer liquid droplets nucleate on the hydrophobic and slippery surface, although they can slide down (or get removed) under gravity (FIG. 3f); and many liquid droplets nucleate and slide down (or get removed) under gravity on the hydrophilic, yet slippery solid surface (FIG. 3g). Due to their enhanced droplet removal, the hydrophilic, yet slippery solid surfaces are anticipated to result in next generation of efficient condenser surfaces with improved heat transfer.

In summary, hydrophilic, yet slippery solid surfaces were fabricated by homogeneous PEGylation of surfaces (i.e., covalently attaching Polyethylene Glycol {PEG} molecules on the surface) in various solvents (such as water, toluene, DMF, etc.). The degree of slipperiness depends on the grafting density of the PEG molecules. The disclosed surfaces are slippery because the PEG molecules were covalently attached to solid substrates (e.g., silicon wafer, glass cover slip etc.) with high degree of chemical homogeneity (i.e., high grafting density) and physical homogeneity (i.e., low surface roughness).

The disclosed hydrophilic (or superhydrophilic), yet slippery solid surfaces have significant applications in enhanced condensation heat transfer, reduced protein adsorption, and biomedical implants and devices (e.g., stents, heart valves, contact lens etc.).

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A hydrophilic and slippery layer comprising an oxygen plasma treated substrate surface covalently bonded to polyethylene glycol brushes via O—Si bonds wherein the substrate surface and the polyethylene glycol brushes form the hydrophilic and slippery layer, the brushes have an inter-tether distance (D) of less than about 20 nanometers, and the surface of the hydrophilic and slippery layer has a root mean square surface roughness ($R_{rms}$) of less than about 10 nanometers.

2. The layer of claim 1 wherein the brushes are a moiety of Formula I:

(I)

wherein
R is —$CH_3$ or —$CH_2CH_3$;
m is 0-2; and
n is 2-1000.

3. The layer of claim 2 wherein n is 6-9.

4. The layer of claim 1 wherein $R_{rms}$ is about 0.1 nanometers to about 0.3 nanometers.

5. The layer of claim 1 wherein the inter-tether distance is less than about 5 nanometers, and a liquid on the surface of the hydrophilic and slippery layer has a sliding angle of less than about 20 degrees.

6. The layer of claim 5 wherein the inter-tether distance is about 1 nanometer to about 3 nanometers.

7. The layer of claim 1 further comprising a hydration layer at the surface of the hydrophilic and slippery layer wherein a liquid on the surface of the hydrophilic and slippery layer has a sliding angle of less than about 15 degrees.

8. The layer of claim 7 wherein the liquid has a surface tension of more than about 30 mN m$^{-1}$.

9. The layer of claim 1 wherein a liquid on the surface of the hydrophilic and slippery layer has a contact angle, sliding angle, or a combination thereof that varies less than about 20% at a relative humidity of about 5% or more.

10. The layer of claim 1 wherein the surface of the hydrophilic and slippery layer resists adsorption or adhesion of a contaminant for about 1 hour or more of exposure to the contaminant.

11. The layer of claim 10 wherein the contaminant comprises a protein.

12. The layer of claim 1 wherein the surface of the hydrophilic and slippery layer is self-lubricating.

13. The layer of claim 1 wherein the hydrophilic and slippery layer is about 60% to about 100% transparent to visible light.

14. A method of forming a hydrophilic and slippery surface comprising the hydrophilic and slippery layer of claim 1 comprising:
  a) immersing a substrate having a hydroxylated surface in a solution consisting essentially of a PEG silane for a sufficient amount of time to covalently bond the PEG silane to the hydroxylated surface to form PEG brushes on the substrate; and
  b) washing the PEG brushes with water to remove excess PEG silane, thereby providing a hydrophilic and slippery surface that has a root mean square surface roughness ($R_{rms}$) of less than about 10 nanometers;
  wherein the hydroxylated surface is covalently bonded to the PEG brushes via O—Si bonds, and the PEG brushes have an inter-tether distance (D) of less than about 20 nanometers.

15. The method of claim 14 wherein the poly(ethylene glycol)silane is grafted to the substrate.

16. The method of claim 14 wherein the poly(ethylene glycol)silane is a 2-[methoxy (polyethyleneoxy)6-9propyl] trialkoxysilane.

17. The method of claim 14 wherein the hydrophilic and slippery surface has a root mean square surface roughness ($R_{rms}$) of about 0.1 nanometers to about 0.3 nanometers.

18. The method of claim 14 wherein the maximum inter-tether distance (D) is less than about 3 nanometers.

19. The method of claim 14 wherein a drop of water on the hydrophilic and slippery surface has a sliding angle ($\omega$) of less than about 10 degrees.

20. A composition comprising the hydrophilic and slippery layer according to claim 1 and a substrate comprising a biomedical implant or device.

21. A method of transferring heat comprising:
  a) condensing an aqueous substance on the surface of the hydrophilic and slippery layer according to claim 1, wherein the condensed aqueous substance forms droplets on the surface of the hydrophilic and slippery layer; and
  b) removing the droplets under an accelerating force;
  wherein the droplets are removed by sliding off the surface of the hydrophilic and slippery layer thereby transferring heat away from the aqueous substance.

22. The method of claim 21 wherein the removal rate of the droplets on the surface of the hydrophilic and slippery layer is faster in comparison to the removal rate of aqueous droplets formed by condensing on hydrophobic and slippery surface, wherein the corresponding coefficient of heat transfer (h) for the surface of the hydrophilic and slippery layer is thereby higher than h for the hydrophobic and slippery surface, and wherein the accelerating force is the same for the comparison.

* * * * *